US006833639B2

United States Patent
Lau et al.

(10) Patent No.: US 6,833,639 B2
(45) Date of Patent: Dec. 21, 2004

(54) ELECTRIC ACTUATOR

(75) Inventors: Collins Yu Cheong Lau, Tsing Yi (HK); Kang Wah Cheung, Tseung Kwan O (HK)

(73) Assignee: Cyber Industrial Ltd., Kowloon Bay (HK)

( * ) Notice: Subject to any disclaimer, the term of this patent is extended or adjusted under 35 U.S.C. 154(b) by 0 days.

(21) Appl. No.: 10/326,116

(22) Filed: Dec. 23, 2002

(65) Prior Publication Data

US 2004/0119344 A1 Jun. 24, 2004

(51) Int. Cl.$^7$ ................................................ H02K 33/04
(52) U.S. Cl. .......................................... 310/36; 310/17
(58) Field of Search ...................... 310/15, 17, 36–38

(56) References Cited

U.S. PATENT DOCUMENTS

| | | | | |
|---|---|---|---|---|
| 3,028,532 A | * | 4/1962 | Favre | 318/132 |
| 3,192,488 A | * | 6/1965 | Faith et al. | 331/154 |
| 3,585,426 A | * | 6/1971 | Newell | 310/49 R |
| 3,668,585 A | * | 6/1972 | Johnson | 336/83 |
| RE31,062 E | * | 10/1982 | Burke, Jr. | 335/229 |
| 4,595,849 A | * | 6/1986 | Cuenoud | 310/36 |
| 4,757,225 A | * | 7/1988 | Wolcott et al. | 310/171 |
| 6,426,576 B1 | * | 7/2002 | Varenne | 310/156.09 |

* cited by examiner

Primary Examiner—Thanh Lam
Assistant Examiner—Judson H. Jones
(74) Attorney, Agent, or Firm—Leydig, Voit & Mayer, Ltd.

(57) ABSTRACT

An electric actuator for providing an angular reciprocating drive, comprising a casing, a stator housed in the casing, and an armature extending co-axially through the stator. The stator has an annular arrangement of poles and a coil for energization by an alternating current to magnetise the poles in opposite polarities as between adjacent poles. The armature has a shaft supported by the casing for angular movement and a plurality of permanent magnets mounted fast on and around the shaft. The magnets have proximal sides as between adjacent magnets of opposite polarities, wherein upon repeated reversals of said alternating current the magnets interact magnetically with the poles to cause the shaft to oscillate thereby providing said drive.

21 Claims, 5 Drawing Sheets

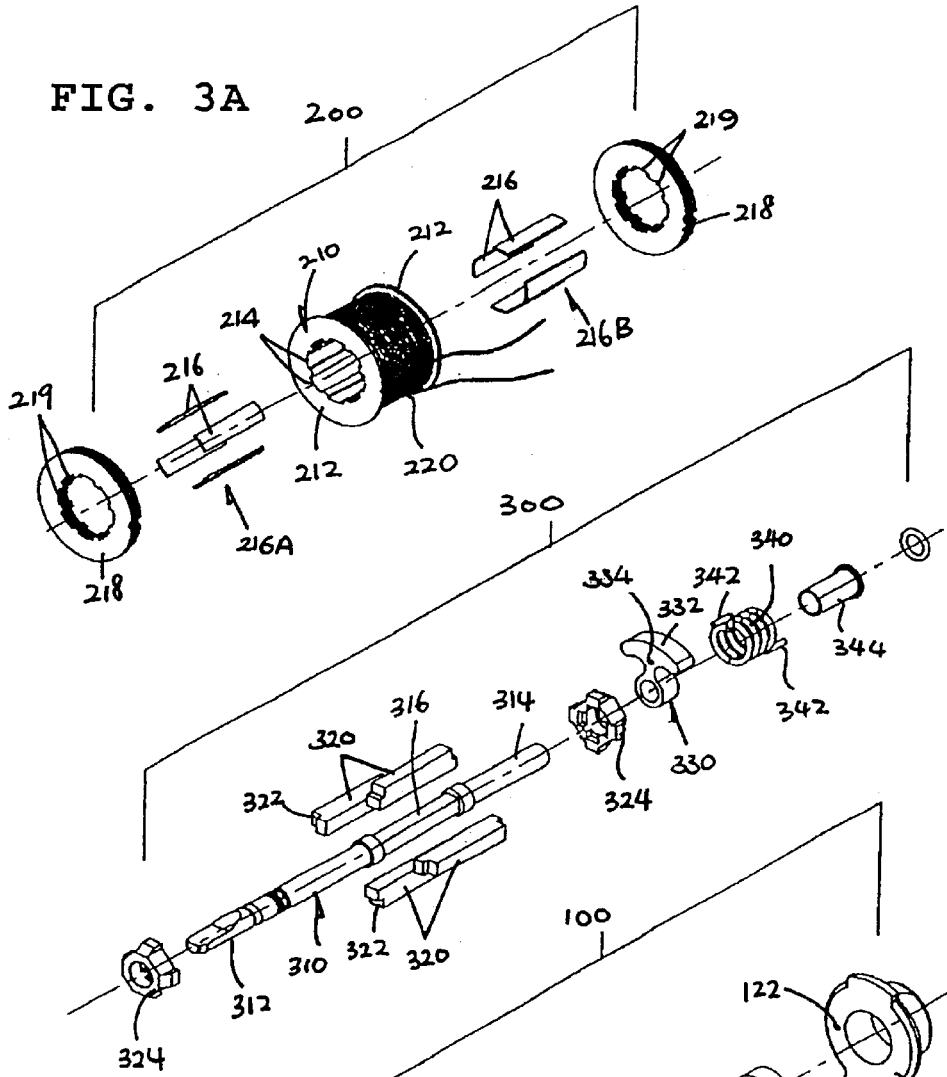
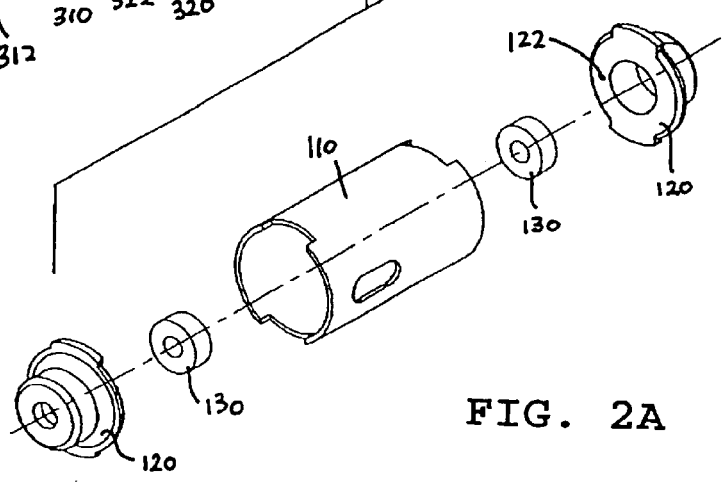

ELECTRIC ACTUATOR

The present invention relates to an electric actuator that provides an angular reciprocating drive for electric hand tools.

BACKGROUND OF THE INVENTION

Angular reciprocating motions are often required in electric hand tools, such as electric toothbrushes in particular. In an electric toothbrush, the reciprocating motion is conventionally and invariably provided by means of an electric motor driving a cam or crank system that translates rotation into reciprocation. There are shortcomings. The cam/crank system represents additional components that have an adverse effect on production cost and mechanical reliability. The indirect transmission of force results in loss of power. Moreover, hygiene is compromised as the cam/crank system introduces inner spaces and corners or the like where stain can build up.

The invention seeks to mitigate or at least alleviate such problems by providing an electric actuator of a novel type.

SUMMARY OF THE INVENTION

According to the invention, there is provided an electric actuator for providing an angular reciprocating drive, comprising a casing, a stator housed in the casing, and an armature extending co-axially through the stator. The stator has an annular arrangement of poles and a coil for energization by an alternating current to magnetise the poles in opposite polarities as between adjacent poles. The armature has a shaft supported by the casing for angular movement and a plurality of permanent magnets mounted fast on and around the shaft. The magnets have proximal sides as between adjacent magnets of opposite polarities, wherein upon repeated reversals of said alternating current the magnets interact magnetically with the poles to cause the shaft to oscillate thereby providing said drive.

Preferably, the magnets are located at equiangular positions around the shaft.

Preferably, each magnet is elongate and extends in substantially the same direction as the shaft.

More preferably, each magnet has a flat surface, and the shaft has a corresponding flat surface against which the magnet lies with its flat surface.

Further more preferably, the magnets are located equiangularly around a section of the shaft, the section having a substantially polygonal cross-section that provides a plurality of flat surfaces positioning the respective magnets.

It is preferred that each magnet has opposite ends and extends substantially parallel to the shaft, and the magnets are secured on the shaft by a pair of mounting members surrounding respective opposite ends of the magnets.

In a preferred embodiment, the poles are divided into two groups each of alternating poles, and the stator includes a pair of ferromagnetic annual members located at opposite ends thereof, each member being connected to a respective group of alternating poles for magnetisation in the same polarity.

More preferably, the poles as between the two groups are shifted in opposite directions for connection with the corresponding annual members.

In a specific construction, the stator includes a spool, around which the coil is wound and inside which the poles are positioned.

More specifically, the spool includes a pair of annual flanges at opposite ends thereof, between which the coil is wound.

More specifically, the spool includes a plurality of grooves on an inner surface thereof, each groove extending axially relative to the spool and locating a respective pole.

It is preferred that the poles and the magnets are arranged in respective equiangular manners, and the number of poles is the same as or an integral multiple of the number of the magnets.

In a preferred embodiment, the armature includes a torsion spring biassing the shaft into a neutral angular position relative to the casing, across which neutral position the shaft is to oscillate.

More preferably, the poles and the magnets are arranged in such a manner that each magnet is positioned symmetrically between a corresponding pair of poles when the shaft is in the neutral position.

More preferably, the spring comprises a coil spring disposed co-axially on the shaft.

More preferably, the spring has a first end engaged with a fixed member on the shaft and a second end engaged with an end cap of the casing.

Further more preferably, the fixed member comprises an eccentric weight mounted fast on the shaft.

It is preferred that the armature includes an eccentric weight mounted fast on the shaft.

It is further preferred that the eccentric weight has a main body extending on a transverse plane of and partially round the shaft.

The invention also provides an electric hand tool incorporating the aforesaid electric actuator, including a body housing the actuator and an implement connectable to an output end of the shaft for driving thereby to reciprocate for operation.

As an example, the electric hand tool is an electric toothbrush, in that the body comprises a handle and the implement comprises a brush head.

BRIEF DESCRIPTION OF DRAWINGS

The invention will now be more particularly described, by way of example only, with reference to the accompanying drawings, in which:

FIG. 2A is an exploded perspective view of the casing of FIG. 2;

FIG. 3A is an exploded perspective view of the solenoid of FIG. 3;

FIG. 4A is an exploded perspective view of the armature of FIG. 4;

DETAILED DESCRIPTION OF PREFERRED EMBODIMENT

Figure 1:
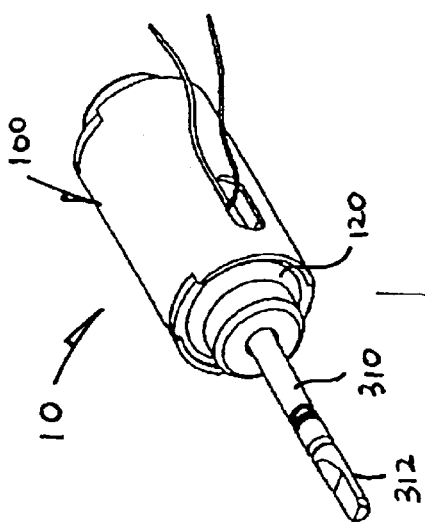
FIG. 1 is a perspective view of an embodiment of an electric actuator in accordance with the invention.
Figure 2:
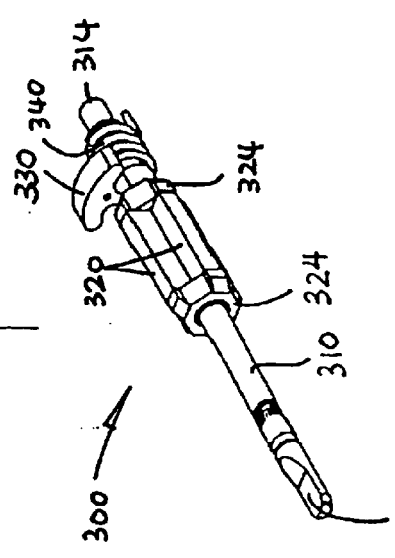
FIG. 2 is a perspective view of a casing of the actuator of FIG. 1.
Figure 4:
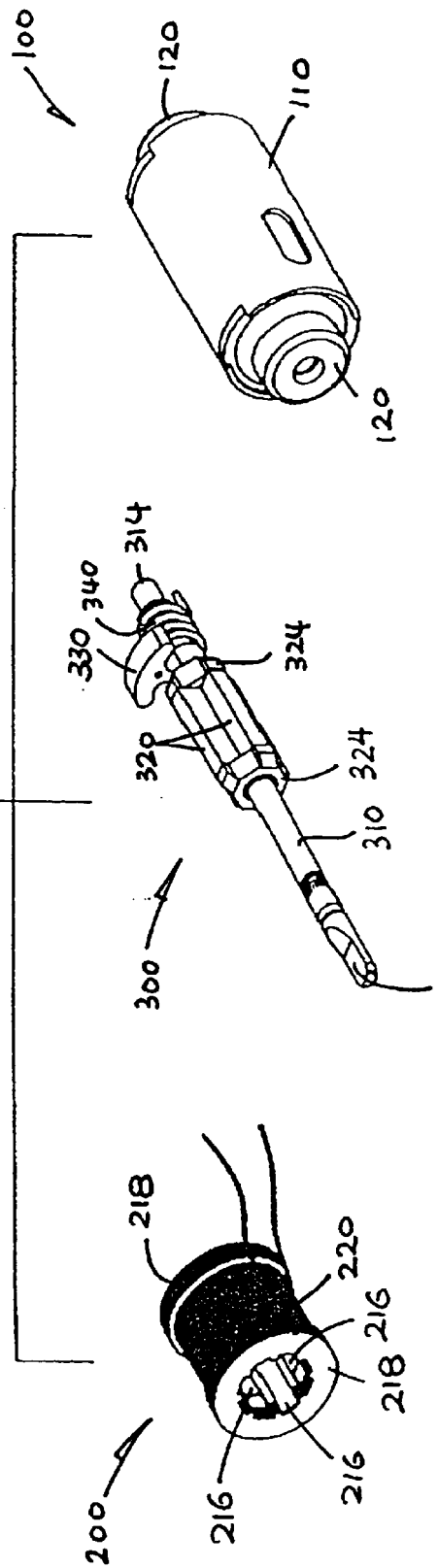
FIG. 4 is a perspective view of an armature of the actuator of FIG. 1, said armature including a shaft and four permanent magnets mounted fast thereon.
Figure 3:
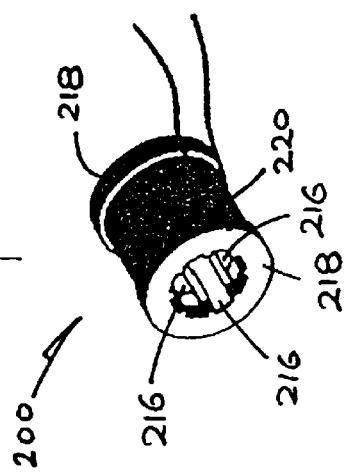
FIG. 3 is a perspective view of a stator solenoid including a coil of the actuator of FIG. 1.

Referring to the drawings, there is shown an electric actuator 10 embodying the invention, which actuator 10 comprises a cylindrical casing 100, a stator solenoid 200 housed co-axially in the casing 100, and an armature 300 extending co-axially through the solenoid 200. Upon energization by an alternating current, the solenoid 200 sets the armature 300 into angular reciprocation for in turn driving an electric hand tool such as an electric toothbrush.

The casing 100 is formed by a double open-ended iron cylinder 110, a pair of circular aluminium end caps 120 closing opposite front and rear ends of the cylinder 110, and a pair of ball bearings 130 located in the centres of the end caps 120 respectively. The rear end cap 120 is formed, at an off-centre position on its inner surface, with a small recess 122.

The stator solenoid 200 comprises a cylindrical aluminium spool 210 having a pair of annular flanges 212 at its opposite ends, and a single coil 220 of enamel copper wire wound co-axially on the spool 210. The coil 220 occupies substantially the entire outer cylindrical space of the spool 210 between its end flanges 212. The inner cylindrical surface of the spool 210 is formed equiangularly with eight straight grooves 214 that extend in the axial direction of the spool 210.

Figure 6:
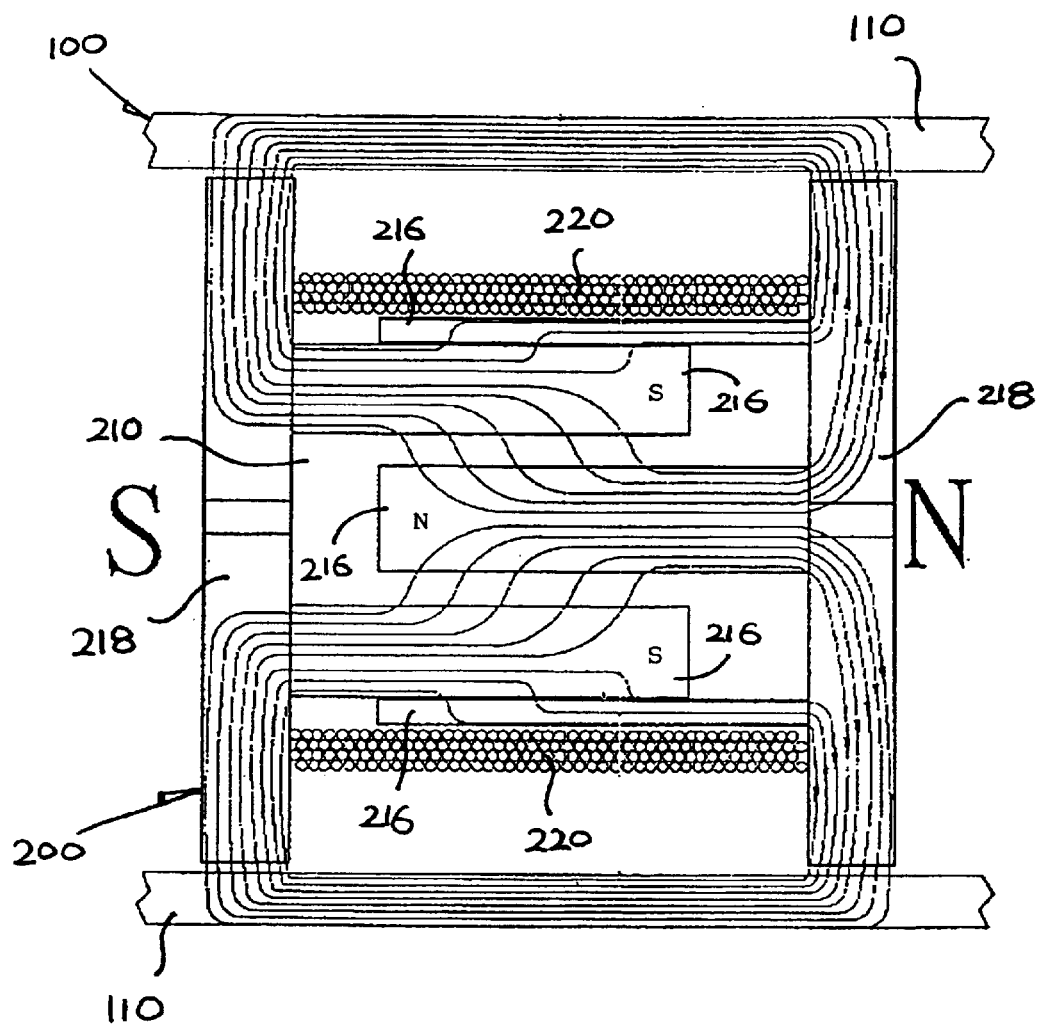
FIG. 6 is a schematic cross-sectional side view of the casing and solenoid of FIGS. 2 and 3, showing a magnetic field generated by the solenoid coil.

Each groove 214 locates a respective ferromagnetic, silicon steel strip acting as a pole 216. The poles 216 are arranged annularly and divided into two groups 216A and 216B of alternating poles 216, each of four poles, which are shifted lengthwise in opposite directions (FIG. 6).

The stator solenoid 200 includes a pair of ferromagnetic laminated flat rings 218, made of silicon steel, which have the same size as and are attached co-axially onto the end flanges 212 respectively. Each end ring 218 has eight equiangularly spaced rectangular teeth 219 around its inner edge. The teeth 219 are aligned with respective grooves 214 of the spool 210 as extensions thereof, with which the poles 216 of the corresponding group 216A/216B shifted to that end are engaged or connected. Thus, each end ring 218 is in contact and hence magnetic circuit with four alternating poles 216 of the group 216A/216B shifted thereto (FIG. 6).

The outer diameter of the spool flanges 212 and end rings 218 should be as large as practically possible compared with the inner diameter of the casing cylinder 110, such that the stator solenoid 200 is housed as a push-fit in the casing 100. Given that the cylindrical wall 110 is in contact with the end rings 218, it acts as a return path for the magnetic flux extending across the two rings 218.

The armature 300 comprises a stainless steel shaft 310 and four permanent magnet bars 320 mounted fast at equiangular positions on and around the shaft 310. The shaft 310 has opposite front and rear ends 312 and 314 journalled through the corresponding bearings 130, with the front end 312 projecting co-axially out of the casing 100 for drive output. Each magnet 320 has a square or rectangular cross-section, including four flat surfaces.

The shaft 310 includes a middle section 316 nearer to the rear end 314, which is of a square cross-section and has the same length as the magnets 320. The middle section 316 provides four flat surfaces, against which the magnets 320 lie respectively with their flat surfaces such that they extend in the same direction as the shaft 310. Each magnet 320 has opposite ends 322 that are stepped. All four magnets 320 are secured in position together on the shaft 310 by a pair of square mounting caps 324, made of zinc alloy, enclosing and grasping the magnet ends 322 at opposite ends of the shaft section 316.

Figure 5:
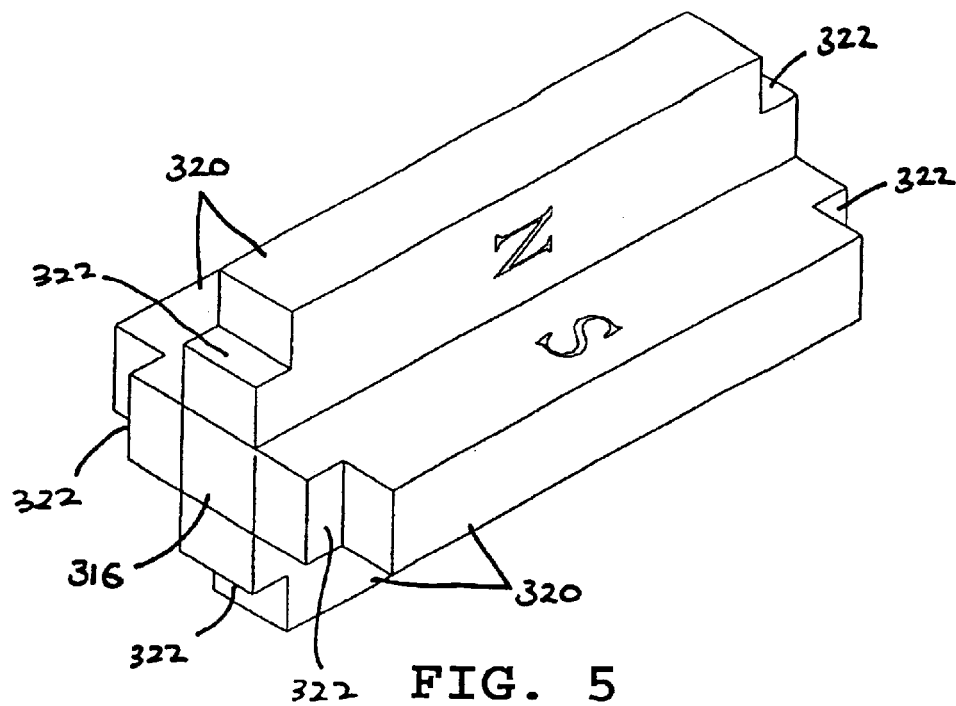
FIG. 5 is a perspective view of the magnets of FIG. 4.
Figure 5A:
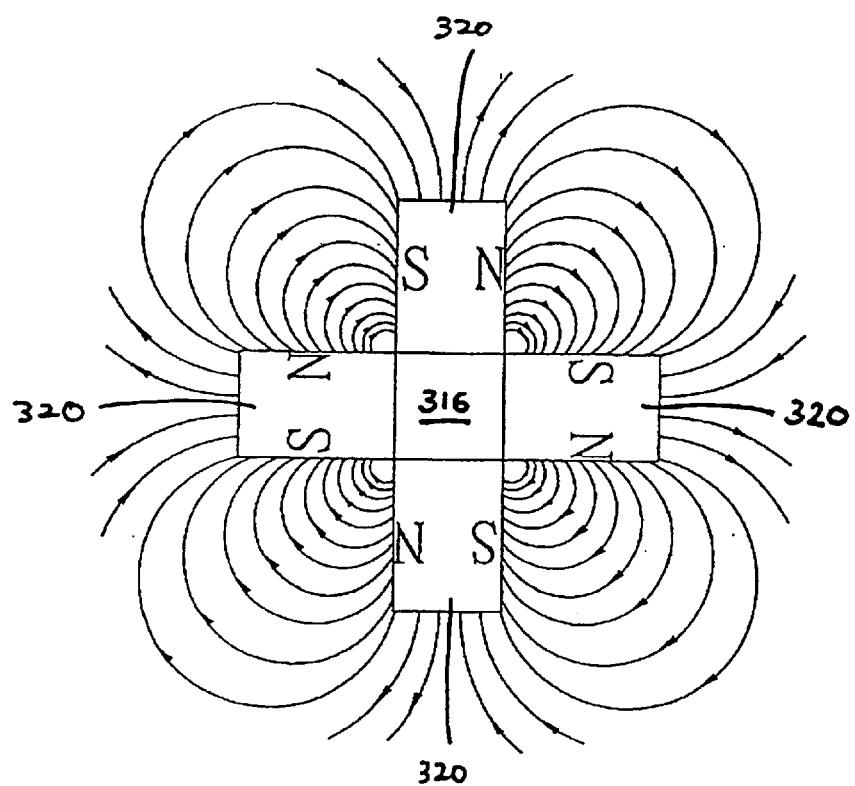
FIG. 5A is a schematic end view showing a magnetic field generated by the magnets of FIG. 5.

The four magnets 320 are high-grade strong magnets made of neodymium ferro boron alloy. They are magnetised and arranged such that their opposing or proximal sides as between the adjacent magnets 320 of each pair are in opposite polarities, thereby producing a magnetic field in the form of four closed loops of magnetic flux as shown in FIG. 5A viewed endwise. The outer diameter of the magnets 320 is marginally smaller than the inner diameter defined by the poles 216, such that the cylindrical air gap between the stator solenoid 200 and the armature 300 is minute to minimise magnetic loss.

The armature 300 includes a T-shaped brass eccentric weight 330 mounted fast on the shaft 310 immediately behind the rear mounting cap 324. A main body 332 of the weight 330 extends in opposite directions on a transverse plane of and partially round the shaft 310, and its stem has a small hole 334. A metal helical coil torsion spring 340, together with a plastic sleeve 344 co-axially therein, is disposed on the rear end 314 of the shaft 310. The spring 340 has opposite ends 342 crooked in opposite axial directions, which engage within the recess 122 of the rear end cap 120 and the hole 334 of the weight 330 respectively. The sleeve 344 separates the spring 340 from contacting the shaft 310.

The spring 340 serves to resiliently bias the shaft 310 into an angular neutral position relative to the rear end cap 120 and hence the casing 100. Under the resilient action of the spring 340, the shaft 310 can only oscillate or reciprocate angularly in opposite directions across the neutral position within a certain angle or amplitude. The weight 330 acts as a counter weight interacting with the spring 340 upon reciprocation of the shaft 310, wherein angular momentum (energy) of the weight 330 is stored in the spring 340 in one direction and then released in the opposite direction.

In operation, the stator coil 220 is to be energized by a symmetrical square-waveform alternating current of a predetermined frequency that falls typically in the range from 50 Hz to 600 Hz and is preferably from 200 Hz to 250 Hz. In either direction (positive or negative half cycle) of the alternating current, the stator solenoid 200 is energized such that its opposite end rings 218 are magnetised in opposite polarities. This results in the two groups 216A and 216B of poles 216, which are connected in an alternating manner to the respective end rings 218, having opposite polarities. That is to say, the polarity of the magnetic field generated by the stator coil 220 changes across adjacent poles 216 of each pair. Upon reversal of the energizing current, the magnetic field and polarities also reverse simultaneously at the same frequency.

While adjacent poles 216 have opposite polarities, the magnetic field of the stator solenoid 200 is as shown in FIG. 6. The magnetic flux flows from one end ring 218, via each of the four poles 216 connected thereto across to the two adjacent poles 216 on its opposite sides, to reach the opposite end ring 218, and then returns via the casing wall 110. The magnetic flux across adjacent poles 216 is laterally bent as a result of the poles 216 having alternating polarities.

Figure 7A:
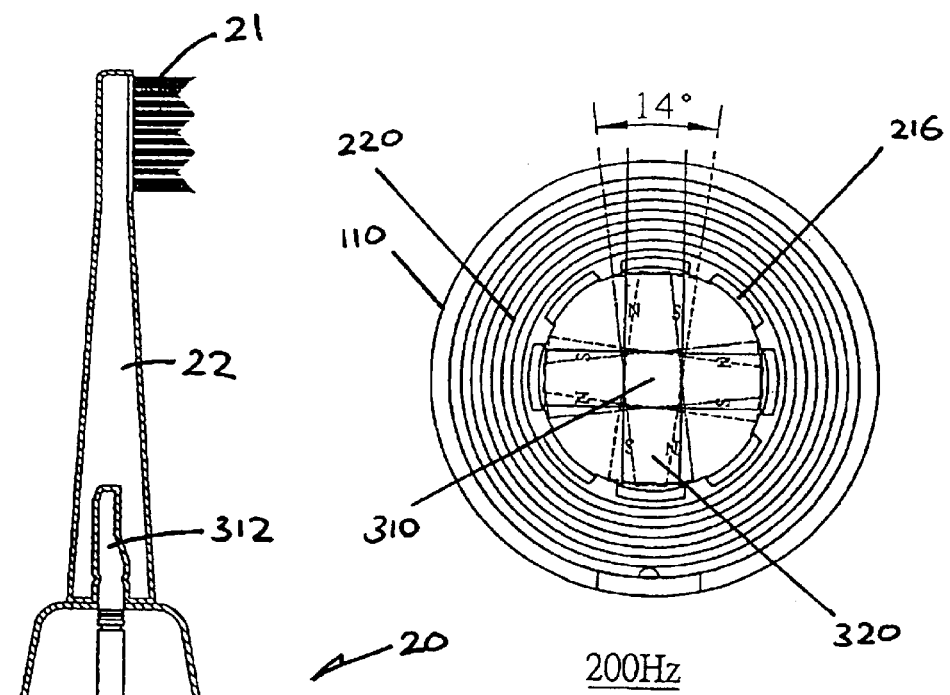
FIG. 7A is a cross-sectional end view of the casing, solenoid and armature of FIGS. 2 to 4, illustrating angular reciprocation of the armature upon the solenoid being energized by an electrical current of 200 Hz.
Figures 7B, 8:
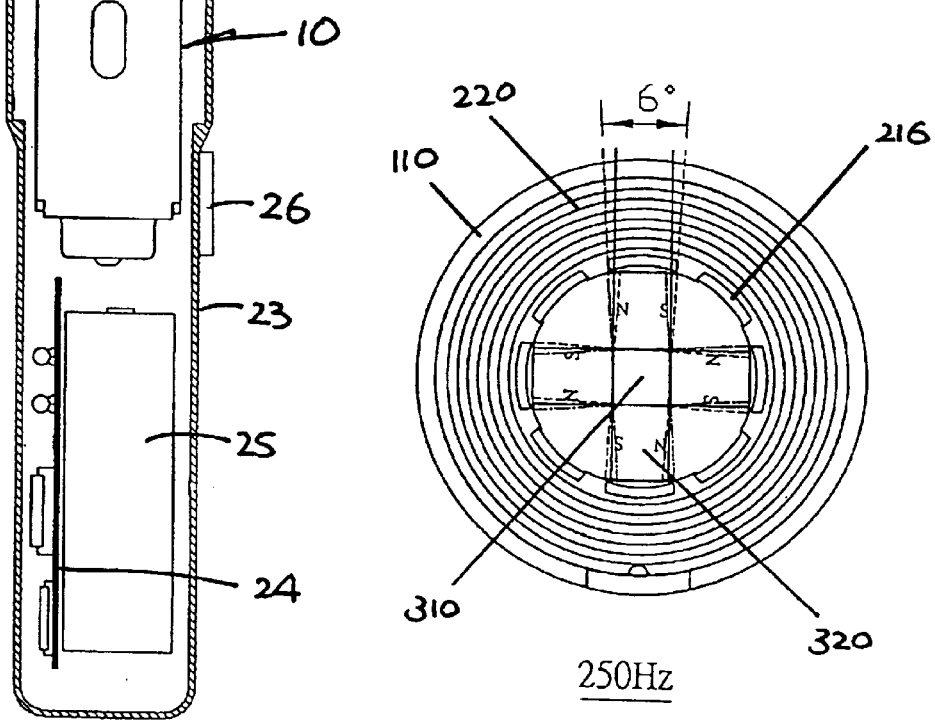
FIG. 7B is a cross-sectional end view corresponding to FIG. 7A, illustrating angular reciprocation of the armature upon the solenoid being energized by an electrical current of 250 Hz.
FIG. 8 is a cross-sectional side view of an electric toothbrush incorporating the actuator of FIG. 1.

The number of poles 216 should be at least the same, or an integral multiple such as two in the case of the described embodiment, as the number of magnets 320, thereby enabling symmetrical angular alignment between them. The spring 340 is angularly arranged such that in the neutral position of the shaft 310 the four magnets 320 are angularly aligned with respective, every other, poles 216 (FIG. 7A or 7B). More specifically, in this position each magnet 320 is positioned symmetrically between a corresponding pair of poles 216, that being the two poles 216 immediately on opposite sides of the pole 216 with which the magnet 320 concerned is aligned.

During a positive half cycle of the energizing current, each magnet 320 is attracted (pulled) by the neighbouring pole piece 216 on one, leading side and simultaneously repelled (pushed) by that on the opposite, trailing side, wherein the armature shaft 310 is turned clockwise for example. As soon as the energizing current reverses to a negative half cycle, the magnets 320 are attracted and repelled in the opposite direction, wherein the shaft 310 is turned anticlockwise. Thus, upon repeated reversals of the energizing current, the shaft 310 oscillates to provide an angularly reciprocating drive at its output end 312.

The amplitude or angle over which the output shaft 310 oscillates is adjustable by changing the frequency of the energizing current in an inverse relationship. For example, the oscillating angle will be about 14° when the energizing current is at 200 Hz frequency (FIG. 7A), or about 6° with a 250 Hz current (FIG. 7B).

An optimal balance should be struck between the amplitude and the torque of the angular motion. The amplitude, in particular, is relatively more important when the subject actuator 10 is used in an electric toothbrush 20 (FIG. 8), as it determines the extent within which a brush head 21 thereof is reciprocated, i.e. the brushing distance.

The brush head 21 is fixed at the front end of a stem 22, whose rear end is releasably coupled onto the output end 312 of the shaft 310 of the actuator 10, for angular oscillation thereby. The toothbrush 20 includes a body in the form of an elongate handle 23 that houses the actuator 10 within its front end and, within its rear end, an electronic control circuit 24 powered by a battery cell 25 to generate the aforesaid energizing current for the actuator 10. A press switch 26 is provided on one side of the handle 23 for switching on and off the actuator 10.

In operation, the brush head 21 swings up and down, rapidly at the same frequency as the energizing current, about the axis of the stem 22 or handle 23 to simulate a conventional manual brushing action.

It should be noted that the interaction between the magnets 320 of the armature 300 and the reversing magnetic field of the stator solenoid 200 does not, in theory, depend on the existence of the torsion spring 340, though its use is preferred. Being in an oscillation system, the spring 340 should be chosen to have a coefficient of elasticity such that resonance will occur in the system at the frequency of oscillation, i.e. that of the energizing current, wherein a maximum amplitude of oscillation is achieved.

It is envisaged that the subject electric actuator 10 may be used in any other types of electric hand tools, such as a rotary grinder or polisher.

The invention has been given by way of example only, and various other modifications of and/or alterations to the described embodiment may be made by persons skilled in the art without departing from the scope of the invention as specified in the appended claims.

What is claimed is:

1. An electric actuator for providing an angular reciprocating drive, comprising:
   a casing;
   a stator housed in the casing; and
   an armature extending co-axially through the stator;
   the stator having an annular arrangement of poles and a coil for energization by an alternating current to magnetise the poles in opposite polarities as between adjacent poles;
   the armature having a shaft supported by the casing for angular movement and a plurality of permanent magnets mounted fast on and around the shaft, wherein each magnet has opposite ends and extends substantially parallel to the shaft, and the magnets are secured on the shaft by a pair of mounting members surrounding respective opposite ends of the magnets;
   the magnets having proximal sides as between adjacent magnets of opposite polarities, wherein upon repeated reversals of said alternating current the magnets interact magnetically with the poles to cause the shaft to oscillate thereby providing said drive.

2. The electric actuator as claimed in claim 1, wherein the magnets are located at equiangular positions around the shaft.

3. The electric actuator as claimed in claim 1, wherein each magnet is elongate and extends in substantially the same direction as the shaft.

4. The electric actuator as claimed in claim 3, wherein each magnet has a flat surface, and the shaft has a corresponding flat surface against which the magnet lies with its flat surface.

5. The electric actuator as claimed in claim 4, wherein the magnets are located equiangularly around a section of the shaft, the section having a substantially polygonal cross-section that provides a plurality of flat surfaces positioning the respective magnets.

6. The electric actuator as claimed in claim 1, wherein the stator includes a spool, around which the coil is wound and inside which the poles are positioned.

7. The electric actuator as claimed in claim 6, wherein the spool includes a pair of annular flanges at opposite ends thereof, between which the coil is wound.

8. The electric actuator as claimed in claim 6, wherein the spool includes a plurality of grooves on an inner surface thereof, each groove extending axially relative to the spool and locating a respective pole.

9. The electric actuator as claimed in claim 1, wherein the poles and the magnets are arranged in respective equiangular manners, and the number of poles is the same as or an integral multiple of the number of the magnets.

10. The electric actuator as claimed in claim 1, wherein the armature includes a torsion spring biassing the shaft into a neutral angular position relative to the casing, across which neutral position the shaft is to oscillate.

11. The electric actuator as claimed in claim 10, wherein the spring comprises a coil spring disposed co-axially on the shaft.

12. An electric hand tool incorporating the electric actuator as claimed in claim 1, including a body housing the actuator and an implement connectable to an output end of the shaft for driving thereby to reciprocate for operation.

13. The electric hand tool as claimed in claim 12, being an electric toothbrush, wherein the body comprises a handle and the implement comprises a brush head.

14. An electric actuator for providing an angular reciprocating drive, comprising:

a casing;

a stator housed in the casing; and an armature extending co-axially through the stator;

the stator having an annular arrangement of poles and a coil for energization by an alternating current to magnetise the poles in opposite polarities as between adjacent poles, wherein the poles are divided into two groups each of alternating poles, and the stator includes a pair of ferromagnetic annular members located at opposite ends thereof, each member being connected to a respective group of alternating poles for magnetisation in the same polarity;

the armature having a shaft supported by the casing for angular movement and a plurality of permanent magnets mounted fast on and around the shaft;

the magnets having proximal sides as between adjacent magnets of opposite polarities, wherein upon repeated reversals of said alternating current the magnets interact magnetically with the poles to cause the shaft to oscillate thereby providing said drive.

15. The electric actuator as claimed in claim 14, wherein the poles as between the two groups are shifted in opposite directions for connection with the corresponding annular members.

16. An electric actuator for providing an angular reciprocating drive, comprising:

a casing;

a stator housed in the casing; and an armature extending co-axially through the stator;

the stator having an annular arrangement of poles and a coil for energization by an alternating current to magnetise the poles in opposite polarities as between adjacent poles, the armature having a shaft supported by the casing for angular movement and a plurality of permanent magnets mounted fast on and around the shaft, the armature including a torsion spring biassing the shaft into a neutral angular position relative to the casing, across which neutral position the shaft is to oscillate, wherein the poles and the magnets are arranged in such a manner that each magnet is positioned symmetrically between a corresponding pair of poles when the shaft is in the neutral position;

the magnets having proximal sides as between adjacent magnets of opposite polarities, wherein upon repeated reversals of said alternating current the magnets interact magnetically with the poles to cause the shaft to oscillate thereby providing said drive.

17. The electric actuator as claimed in claim 10, wherein the spring has a first end engaged with a fixed member on the shaft and a second end engaged with an end cap of the casing.

18. An electric actuator for providing an angular reciprocating drive, comprising:

a casing;

a stator housed in the casing; and an armature extending co-axially through the stator;

the stator having an annular arrangement of poles and a coil for energization by an alternating current to magnetise the poles in opposite polarities as between adjacent poles, the armature having a shaft supported by the casing for angular movement and a plurality of permanent magnets mounted fast on and around the shaft, the armature including a torsion spring biassing the shaft into a neutral angular position relative to the casing, across which neutral position the shaft is to oscillate, wherein the spring has a first end engaged with a fixed member on the shaft and a second end engaged with an end cap of the casing and wherein the fixed member comprises an eccentric weight mounted fast on the shafts;

the magnets having proximal sides as between adjacent magnets of opposite polarities, wherein upon repeated reversals of said alternating current the magnets interact magnetically with the poles to cause the shaft to oscillate thereby providing said drive.

19. An electric actuator for providing an angular reciprocating drive, comprising:

a casing;

a stator housed in the casing; and an armature extending co-axially through the stator;

the stator having an annular arrangement of poles and a coil for energization by an alternating current to magnetise the poles in opposite polarities as between adjacent poles, the armature having a shaft supported by the casing for angular movement and a plurality of permanent magnets mounted fast on and around the shaft, wherein the armature includes an eccentric weight mounted fast on the shaft;

the magnets having proximal sides as between adjacent magnets of opposite polarities, wherein upon repeated reversals of said alternating current the magnets interact magnetically with the poles to cause the shaft to oscillate thereby providing said drive.

20. The electric actuator as claimed in claim 19, wherein the eccentric weight has a main body extending on a transverse plane of and partially round the shaft.

21. An electric actuator for providing an angular reciprocating drive, comprising:

a casing;

a stator housed in the casing; and an armature extending co-axially through the stator;

the stator having an annular arrangement of poles and a coil for energization by an alternating current to magnetise the poles in opposite polarities as between adjacent poles;

the armature having a shaft supported by the casing for angular movement and a plurality of permanent magnets mounted fast on and around the shaft;

the magnets having proximal sides as between adjacent magnets of opposite polarities, the adjacent magnets each having opposite sides of opposite polarities, wherein upon repeated reversals of said alternating current the magnets interact magnetically with the poles to cause the shaft to oscillate thereby providing said drive.

* * * * *